United States Patent
Song et al.

(10) Patent No.: US 10,603,404 B2
(45) Date of Patent: Mar. 31, 2020

(54) PHOSPHAZENE-BASED POLYMER FOR TISSUE ADHESION, A METHOD FOR PREPARING THE SAME, AND USE THEREOF

(71) Applicant: KOREA INSTITUTE OF SCIENCE AND TECHNOLOGY, Seoul (KR)

(72) Inventors: Soo Chang Song, Seoul (KR); Young-Min Kim, Seoul (KR); ChangHo Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 18 days.

(21) Appl. No.: 15/809,022

(22) Filed: Nov. 10, 2017

(65) Prior Publication Data
US 2018/0133362 A1    May 17, 2018

(30) Foreign Application Priority Data
Nov. 11, 2016    (KR) .................. 10-2016-0150503

(51) Int. Cl.
*A61L 26/00* (2006.01)
*A61L 24/04* (2006.01)
*C08G 79/025* (2016.01)

(52) U.S. Cl.
CPC ......... *A61L 26/0014* (2013.01); *A61L 24/046* (2013.01); *C08G 79/025* (2013.01); *A61L 2400/04* (2013.01)

(58) Field of Classification Search
CPC ............... A61L 26/0014; A61L 24/046; A61L 2400/04; A61L 24/0031; C08G 79/025; C08L 85/02
USPC ......................................................... 528/321
See application file for complete search history.

(56) References Cited

U.S. PATENT DOCUMENTS

| | | | | |
|---|---|---|---|---|
| 4,221,898 A | * | 9/1980 | Hergenrother | C08G 79/025 528/168 |
| 6,319,984 B1 | * | 11/2001 | Song | C08G 79/025 525/54.1 |
| 7,598,318 B2 | * | 10/2009 | Sohn | C08G 69/42 525/419 |
| 2005/0020808 A1 | * | 1/2005 | Song | A61K 9/0024 528/492 |
| 2009/0047348 A1 | * | 2/2009 | Song | A61K 31/56 424/486 |
| 2010/0297155 A1 | * | 11/2010 | Song | A61K 9/06 424/184.1 |
| 2013/0004455 A1 | * | 1/2013 | Song | A61L 27/18 424/78.17 |
| 2014/0031289 A1 | * | 1/2014 | Song | C08G 79/025 514/11.4 |
| 2016/0129149 A1 | * | 5/2016 | Elisseeff | A61L 24/0031 514/54 |

FOREIGN PATENT DOCUMENTS

| | | |
|---|---|---|
| KR | 100259367 B1 | 6/2000 |
| KR | 100315630 B1 | 12/2001 |
| KR | 1020090051141 A | 5/2009 |
| KR | 1020130034382 A | 4/2013 |

OTHER PUBLICATIONS

Young-Min Kim et al., "Development of an Injectable Dopamine-conjugated Poly(organophophazene) Hydrogel for Hemostasis", Bulletin of the Korean Chemical Society, 2016, pp. 372-377, vol. 37, Korean Chemical Society, Seoul & Wiley-VCH Verlag GmbH & Co. KGaA, Weinheim.

* cited by examiner

*Primary Examiner* — Douglas J Mc Ginty
(74) *Attorney, Agent, or Firm* — Cantor Colburn LLP

(57) ABSTRACT

The present invention relates to a phosphazene-based polymer comprising an amino acid ester, polyethylene glycol, a group comprising a functional group, and a catechol group linked directly or by a linker to a part of or an entire functional group, in a predetermined ratio. In addition, the present invention relates to a preparation method thereof, and a tissue-adhesive composition comprising the same as an active ingredient.

18 Claims, 6 Drawing Sheets

PHOSPHAZENE-BASED POLYMER FOR TISSUE ADHESION, A METHOD FOR PREPARING THE SAME, AND USE THEREOF

TECHNICAL FIELD

The present invention relates to a phosphazene-based polymer comprising an amino acid ester, polyethylene glycol, a group comprising a functional group, and a catechol group linked directly or by a linker to a part of or an entire functional group, in a predetermined ratio. In addition, the present invention relates to a preparation method thereof, and a tissue-adhesive composition comprising the same as an active ingredient.

BACKGROUND ART

Tissue-adhesive substances can be applied not only to various medical fields such as wound healing, adhesion of surgical tissue, hemostasis, etc., but also to a drug-delivery system and tissue regeneration, and therefore, the possibility of its potential utilization is highly evaluated. Representative tissue-adhesive substances include a fibrin adhesive or a cyanoacrylate-based substance, but since problems associated with concerns of infection and toxicity have occurred, it is necessary to discover safe substances exhibiting excellent tissue adhesiveness. Additionally, because most tissue-adhesive substances currently in use are sensitive to moisture, adhesion strength of substances containing adhesiveness may significantly be decreased depending on the application environment. In particular, the adhesiveness tends to be deteriorated, lost, or desorbed at the time of application to a living body, and therefore, there is a possibility that frequent reapplication of tissue-adhesive substances is required.

A temperature-sensitive hydrogel shows a sol-gel phase transition in which a liquid state, e.g., a sol form, is maintained at a low temperature but converts into a gel as the temperature rises. This is advantageous in that since a temperature-sensitive hydrogel is injected in a liquid form, the hydrogel can be evenly distributed to a lesion even if tissues therein to be applied exist in any shape, and immediately forms a gel having a three-dimensional structure due to body temperature. Accordingly, it can effectively exist in a form suitable for an application site, thereby having a potential as a tissue-adhesive substance. In addition, it is advantageous in that the hydrogel can be treated by mixing with various substances that are useful for tissue adhesion. However, it is known that the temperature-sensitive hydrogel has difficulty in a clinical application due to low tissue adhesiveness, strength, and rapid loss.

The present inventors found from previous studies that phosphazene-based polymers obtained by substituting a dichlorophosphazene linear polymer with an amino acid ester and methoxypolyethylene glycol exist in a liquid state below a certain temperature. However when the temperature exceeds a certain temperature, it was confirmed that the phosphazene-based polymers retained a property as a temperature-sensitive polymer which exhibits a sol-gel phase transition in a gel form having a three-dimensional structure (Korean Patent Nos. 10-0259367 and 10-0315630).

On the other hand, in the case of catechol, which occupies the majority of adhesion proteins extracted from mussels, it not only has resistance against moisture but also exhibits strong adhesion, excellent resilience, and no toxicity. Therefore, there has been an increase in the possibility of applying the catechol as an adhesive substance. Furthermore, research on a hydrogel having adhesiveness by using the above tendencies has also been reported.

Accordingly, the present inventors made extensive efforts to discover temperature-sensitive and tissue-adhesive polymers with improved adhesiveness of tissues by modifying phosphazene-based polymers having biodegradability and temperature-sensitivity. As a result, it was confirmed that polymers in which a moiety having a functional group in addition to an amino acid ester and methoxypolyethylene glycol is introduced followed by linking a catechol group at a predetermined ratio exhibited a sol-gel transition at a temperature near the body temperature. Therefore, it was also confirmed that it causes the polymers to be converted into a hydrogel form while enhancing the adhesiveness of tissues so that a polymer hydrogel with improved adhesion of a wound can be provided when applied to a human body, thereby completing the present invention.

DISCLOSURE

Technical Problem

An object of the present invention is to provide a phosphazene-based polymer comprising a catechol group, wherein on a phosphorous atom of a polyphosphazene backbone, a first moiety of an amino acid ester; a second moiety of polyethylene glycol; a third moiety comprising a functional group; and a fourth moiety comprising a catechol group linked directly or by a linker to a part of or an entire functional group of the third moiety are linked by —O— or —NH— in a predetermined molar ratio.

Another object of the present invention is to provide a preparation method of the phosphazene-based polymer comprising a catechol group.

Yet another object of the present invention is to provide a tissue-adhesive composition comprising the phosphazene-based polymer comprising a catechol group as an active ingredient.

Technical Solution

As an aspect to achieve the above objects, the present invention provides a phosphazene-based polymer comprising a catechol group, wherein on a phosphorous atom of a polyphosphazene backbone represented by the following Formula 1, a first moiety of an amino acid ester represented by the following Formula 2; a second moiety of polyethylene glycol represented by the following Formula 3; a third moiety comprising a functional group; and a fourth moiety comprising a catechol group linked directly or by a linker to a part of or an entire functional group of the third moiety are linked by —O— or —NH— in a molar ratio of a:b:c:d, respectively:

[Formula 1]

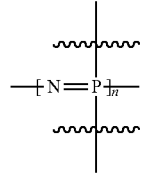

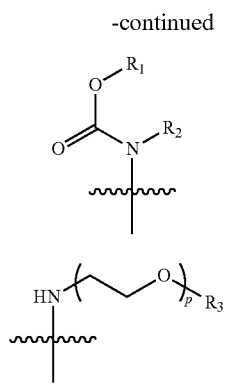

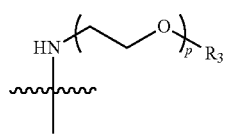

wherein, the sum of a and b, and c and d is each independently 5 mol % to 90 mol %; and the c:d ratio is in a range of 1:0.1 to 1:1;

and wherein, in Formulas 1, 2, and 3, $R_1$ is $C_{1-6}$ alkyl, $C_{1-6}$ alkenyl, or $C_{6-10}$ aryl-$C_{1-6}$ alkyl;

$R_2$ is hydrogen, methyl, isopropyl, 1-methylpropyl, 2-methylpropyl, thiomethyl, methylthioethyl, benzyl, hydroxylbenzyl, or 2-indolylmethyl;

$R_3$ is $C_{1-6}$ alkyl;

n is an integer of 3 to 100,000; and p is an integer of 1 to 20.

Specifically, in the above Formulas 1, 2, and 3, a may be 55 mol % to 77 mol %; b may be 5 mol % to 30 mol %; and a sum of c and d may be 10 mol % to 20 mol %, but a, b, c, and d are not limited thereto.

For example, in the phosphazene-based polymer comprising a catechol group according to the present invention, the functional group may be a hydroxy group or a carboxy group, but is not limited thereto.

For example, n may be an integer of 100 to 10,000, but is not limited thereto.

For example, the second moiety of polyethylene glycol may be a polymer moiety having a weight average molecular weight of 300 to 3,000 such that the final polymer has biodegradability and temperature-sensitivity, but is not limited thereto.

For example, in the phosphazene-based polymer comprising a catechol group according to the present invention, $R_1$ may be methyl, ethyl, propyl, butyl, benzyl, or 2-propenyl; and $R_3$ may be methyl, but these are not limited thereto.

For example, the phosphazene-based polymer comprising a catechol group according to the present invention may be a polymer having a weight average molecular weight of 500 to 100,000. For example, it may be a polymer having a weight average molecular weight of 1,000 to 50,000, but is not limited thereto.

Additionally, the phosphazene-based polymer comprising a catechol group according to the present invention may further comprise a fifth moiety, in which at least one functional substance selected from the group consisting of a substance capable of regulating decomposition rate of a polymer, a substituent comprising an ionic group capable of regulating decomposition rate, a substituent capable of cross-linking, an additional compound capable of inducing tissue adhesion, a physiologically active substance, and a composite material formed by liner connection of two or more substances among them is linked directly or by a linker to a part of or an entire functional group of the third moiety.

Further, the functional group and/or the functional substance linked thereto may be in a form protected by a protecting group.

A non-limiting example of the substance capable of regulating the decomposition rate of a polymer may comprise amino acids, peptides, and depsipeptide esters.

The substituent comprising an ionic group capable of regulating the decomposition rate may be a substituent comprising a dicarboxylic acid-based compound having 3 to 30 carbon atoms, specifically 3 to 9 carbon atoms, more specifically 3 to 6 carbon atoms, which is linked via a hydroxy group-containing divalent functional group, or $NH_2CH(SH)CO_2H$, $NH_2(CH_2)_qSH$, $NH_2(CH_2CH_2NH)_rH$, $[NH_2CH(C_4H_8NH_2)CO]_rOH$, $[NH_2CH[(CH_2)_3C(=NH)(NH_2)]CO]_rOH$, $[OCH_2CH_2CH_2CH_2CH_2N(CH_2CH_2CO_2CH_2CH_2)_2]_r$, folic acid, hyaluronic acid, cyclodextrin, an imidazole-based compound, an anticancer agent, histidine, lysine, arginine, cysteine, thioalkylamine (e.g., having 1 to 50 carbon atoms), spermine, or spermidine which are additionally linked thereto, or polyethyleneimine, polyhistidine, polylysine, polyarginine having various weight average molecular weights, or comprising protamine, heparin, chitosan, protamine, or a peptide comprising 1 to 20 amino acids, e.g., an RGD or RGD derivative which is a peptide consisting of 4 to 5 amino acids comprising RGD, e.g., RGDS, RGDY, GRGDS, GRGDY, etc.).

The substituent capable of cross-linking may include a substituent capable of forming a chemical cross-link and/or a cross-link caused by ultraviolet radiation, a cross-linking agent, and/or the presence of an additive and enzyme, without limitation. For example, the substituent capable of cross-linking may be a compound having a thiol group or a vinyl group, or a compound having tyramine, tyrosine, or phenyl derivatives, such as an acrylate-based compound, a methacrylate-based compound, an acrylamide-based compound, a vinylsulfone-based compound, a thiol-based compound, a cysteine-based compound, a cysteamine-based compound, a mercaptic acid-based compound, and an allyl pyrimidine-based compound.

The additional compound capable of inducing tissue adhesion may be a constituent comprising a cyanoacrylate-based compound used as a functional group for conventional tissue adhesion.

The physiologically active substance may be a drug, such as a protein, a polypeptide, a peptide, an antibody, a fusion protein, a hormone, a vaccine, a gene, an anticancer agent, or an angiogenesis inhibitor, but is not limited thereto.

Another aspect of the present invention provides a preparation method of the phosphazene-based polymer comprising a catechol group according to the present invention, comprising: a first step of reacting poly(dichlorophosphazene) of Formula 4 with an (amino acid)($C_{1-6}$ alkyl)ester of Formula 5; a second step of reacting the reaction mixture obtained from the previous step by adding amino($C_{1-6}$ alkoxy)polyethylene glycol and amino($C_{1-6}$ alkanol); a third step of reacting the reaction mixture of the previous step by further adding a amino($C_{1-6}$ alkoxy)polyethylene glycol solution dropwise; a fourth step of reacting the product obtained from the previous step with $C_{1-6}$ alkanedioic acid or an anhydride thereof, and dimethylaminopyridine; and a fifth step of reacting the product obtained from the previous step with di($C_{1-6}$ alkyl)carbodiimide, hydroxysuccinimide, and dopamine:

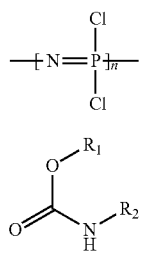

[Formula 4]

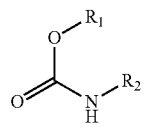

[Formula 5]

wherein, in Formulas 4 and 5, $R_1$, $R_2$, and n are as defined above.

In the preparation method of the catechol group-containing phosphazene polymer of the present invention, an (amino acid)($C_{1-6}$ alkyl)ester moiety, alkoxypolyethylene glycol, and a hydroxyalkyl group can be introduced into a polyphosphazene backbone through the first to third steps.

For example, the first to third steps may be carried out in a tetrahydrofuran solution in the presence of triethylamine, but are not limited thereto.

For example, the tetrahydrofuran selected as a solvent can dissolve all reactants used, and accordingly, a homogeneous solution which improves the reaction efficiency can be provided. Therefore, the solvent which can be used is not limited to tetrahydrofuran, and various solvents known in the art may be used without limitation as long as all of the reactants used are efficiently and completely dissolved.

Additionally, the reaction may be carried out by including triethylamine, and thus problems caused by an occurrence of chlorine gas can be prevented because triethylamine holds chlorine gas generated during the reaction. This is merely an example, and the reaction is not limited to only triethylamine. That is, various substances may be used as long as the substances can hold chlorine gas during the reaction.

For example, the first step may be carried out for 24 hours to 60 hours while increasing a temperature from a range of −80° C. to −50° C. to a range of 10° C. to 50° C., but is not limited thereto.

Since the (amino acid)($C_{1-6}$ alkyl)ester, the reactant of the first step, exhibits very high reactivity with a polyphosphazene backbone, it reacts intensely even at room temperature so that it does not evenly bind to polymers in general; instead, it agglomerates with polymers to be bound with one another. Accordingly, uneven bonding caused by such explosive reaction can be prevented by initiating the reaction at a low temperature of −80° C. to −50° C. Thereafter, the temperature can be increased to 10° C. to 50° C. as the reaction progresses, thereby allowing the remaining reactants to be completely reacted.

The reaction time is not limited as long as the reaction can sufficiently be carried out, and can appropriately be adjusted according to the reaction temperature. For example, if the reaction time is short, reactants may remain because a reaction is not completed, whereas time and/or energy may be unnecessarily wasted with longer reaction times.

For example, the second and third steps may be independently carried out at 35° C. to 60° C. for 24 hours to 60 hours, but are not limited thereto. Alternately, the second and third steps may be further carried out for 24 hours at room temperature and 24 hours at 40° C. to 50° C., respectively, while adjusting the temperature in two stages, but are not limited thereto.

As described above, in order to prevent uneven reaction caused by an explosive reaction while ultimately allowing reactants to be completely reacted, the reaction can be completed by reacting the same at a relatively low temperature for a certain period of time, followed by progressing the additional reaction by raising the temperature.

In order to improve yield and purity of a product, and to efficiently carry out the reaction, the third step may further carry out a step of filtering the resulting reaction mixture; concentrating the filtrate under reduced pressure; dissolving the resulting mixture in methanol; and dialyzing the resulting mixture with methanol and water. The dialysis may be independently carried out for 3 days to 7 days, e.g., 5 days, with each solvent, but is not limited thereto.

For example, the fourth step may be carried out in a dry tetrahydrofuran solution at 35° C. to 60° C. for 5 hours to 36 hours, but is not limited thereto. As in the previous steps, in the fourth step, the reaction temperature and/or the reaction time may appropriately be adjusted in consideration of the reactivity between each reactant and a polyphosphazene backbone and/or the reaction completeness.

As in the third step, in order to improve yield and purity of a product, and to efficiently carry out the reaction, the fourth step may further carry out a step of filtering the obtained reaction mixture; concentrating the filtrate under reduced pressure; dissolving in methanol; and dialyzing the resulting concentrate with methanol and water after the reaction of the fourth step. The dialysis may be independently carried out for 3 days to 7 days, for example, 5 days, with each solvent, but is not limited thereto.

For example, the fifth step may be carried out in a dry dimethylformamide solution at 10° C. to 35° C., but is not limited thereto.

For example, the fifth step may be carried out by sequentially adding di($C_{1-6}$ alkyl)carbodiimide, hydroxysuccinimide, and dopamine while reacting for 10 minutes to 60 minutes, 12 hours to 36 hours, and 24 hours to 72 hours, respectively, but is not limited thereto.

For example, the (amino acid)($C_{1-6}$ alkyl)ester may be isoleucine ethyl ester; the amino($C_{1-6}$ alkoxy)polyethylene glycol may be amino methoxypolyethylene glycol; the $C_{1-6}$ aminoalkanol may be aminoethanol; the $C_{1-6}$ alkanedioic acid or the anhydride thereof may be succinic acid, glutaric acid, adipic acid, or an anhydride thereof; and di($C_{1-6}$ alkyl)carbodiimide may be diisopropylcarbodiimide.

Another aspect of the present invention provides a tissue-adhesive composition comprising the catechol group-containing phosphazene-based polymer of the present invention as an active ingredient.

For example, the composition may be used for hemostasis.

For example, the composition may be converted from a sol form to a gel form due to body temperature.

For example, the tissue-adhesive composition may be in a form of a polymer solution in which the catechol group-containing phosphazene-based polymer of the present invention is dissolved in a solvent, e.g., water, a buffer solution, an acidic solution, a basic solution, a salt solution, physiological saline, water for injection, dextrose saline, etc., at the concentration of 1 wt % to 50 wt %, preferably 3 wt % to 20 wt %.

In the specific exemplary embodiments of the present invention, it was confirmed that the catechol group-containing phosphazene-based polymers prepared to contain each moiety in various compositions according to the present invention began to increase in viscosity at around 30° C., which is a temperature below body temperature. That is, gelation of the catechol group-containing phosphazene-based polymers started. Therefore, it was confirmed that when applied to a wounded area, they gelled to form a hydrogel due to body temperature immediately after adhering to a lesion by tissue adhesion, and thus bleeding from the wounded area can be dramatically reduced. In addition, it was confirmed that although the amount thereof was slightly decreased after 2 weeks of application in the body, the catechol group-containing phosphazene-based polymers were still maintained in the form of a gel while adhering to the wounded area.

Therefore, since the tissue-adhesive composition of the present invention has an excellent hemostatic effect, it exhibits superior tissue adhesiveness even if it is directly applied to a bleeding site having high moisture, and thus such tissue-adhesive composition can be effectively used as a hemostatic adhesive substance. In addition, because the tissue-adhesive composition of the present invention covers a wounded area and forms a hydrogel membrane, it prevents the wounded area from being exposed to an external environment while protecting the same, and therefore, it not only prevents an infection but also promotes wound healing.

Therefore, the tissue-adhesive composition of the present invention can be effectively used as a biomaterial inserted in the body, e.g., wound-suture materials used for reconstruction surgery or after surgery; surgical materials used for wound treatment, mucosal closure, perforation surgery, organ rupture, etc.; ophthalmic materials used for conjunctiva, cornea, cataract, and refractive surgeries; support materials used for fixing dental implants, transplanted organs, and fistula restoration, etc.; and biomaterials which require sufficient gel strength for hemostatic materials used in emergency, plastic surgery materials that maintain a long-term shape thereof, etc. In addition, since a polymer containing a fifth moiety in which physiologically active substances, such as drugs, etc., are linked by a covalent bond can release a drug by breaking the bond, the release of the drug can be delayed. Accordingly, the polymer has an advantage in that a drug can be continuously released compared with a hydrogel containing a simple mixed drug. In addition, as described above, because the polymer of the present invention has tissue adhesiveness, it may act advantageously on efficient topical delivery of an additionally loaded physiologically active substance.

Advantageous Effects

Since the catechol group-containing phosphazene-based polymer of the present invention has temperature sensitivity and tissue adhesiveness, it becomes a gel when applying the same to a lesion in a liquid form due to body temperature. Accordingly, it can be effectively applied to a lesion, without loss of the composition. In particular, a catechol group is less sensitive to moisture and exhibits superior tissue adhesiveness even at a bleeding site, and thus can be directly applied to the site of wound accompanying bleeding or to a lesion after surgery. Accordingly, the catechol group-containing phosphazene-based polymer of the present invention can prevent infection while promoting wound healing.

BRIEF DESCRIPTIONS OF THE DRAWINGS

DETAILED DESCRIPTION OF THE EMBODIMENT

Figure 1:
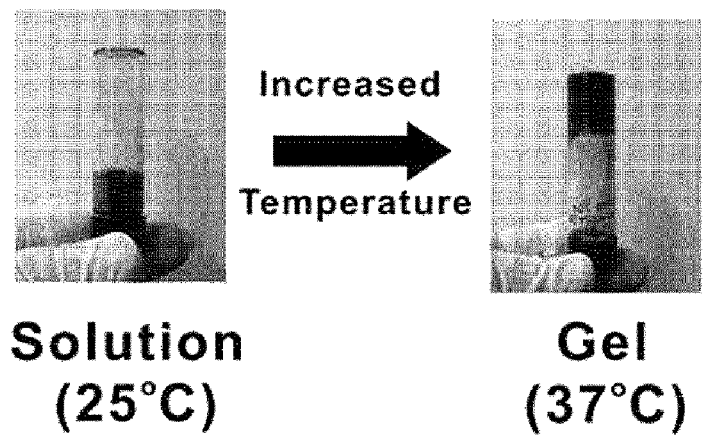
FIG. 1 is a photograph showing a sol-gel transition behavior depending on a temperature change of the catechol group-containing phosphazene-based polymer of the present invention.

Hereinbelow, the present invention will be described in detail with accompanying exemplary embodiments. However, the exemplary embodiments disclosed herein are only for illustrative purposes and should not be construed as limiting the scope of the present invention.

<Identification of Compounds>

In the exemplary embodiments below, the elemental analysis of carbon, hydrogen, and nitrogen was carried out using Perkin-Elmer's C, H, and N analyzers in the Advanced Analysis Center at the Korea Institute of Science and Technology (KIST), in order to identify synthesized polymers. In addition, the nuclear magnetic resonance spectrum with hydrogen and phosphorous was measured by using a Varian Gemini-300, and the average molecular weight ($M_w$) was measured though gel permeation chromatography using a Waters 1515 pump and a 2410 differentiation refractometer.

Example 1: Preparation of Poly[(Isoleucine Ethyl Ester)$_{1.21}$(Amino Methoxypolyethylene Glycol 750)$_{0.51}$(Amino Ethylsuccinate)$_{0.22}$(Aminoethyl Dopamine)$_{0.06}$Phosphazene]$_n$ Step 1: Dry isoleucine ethyl ester hydrochloride (IleOEt.HCl, 9.79 g, 50.04 mmol) was dissolved in 100 mL of anhydrous tetrahydrofuran (THF), followed by addition of triethylamine (24.41 g, 175.17 mmol). Poly(dichlorophosphazene) (4.00 g, 34.52 mmol) dissolved in anhydrous tetrahydrofuran (50 mL) was added dropwise to the mixed solution in an acetone-dry ice bath at −60° C., and then gradually raised to room temperature, thereby reacting the resultant for 48 hours.

Step 2: After confirmation of the progress of the reaction in Step 1 while confirming $^{31}$P-NMR, dry aminoethanol (0.62 g, 10.35 mmol) was dissolved in anhydrous tetrahydrofuran (50 mL), and triethylamine was added thereto so that the resultant was added to the above reactant. Thereafter, a solution, in which triethylamine (4.21 g, 30.20 mmol) was added to dry amino methoxypolyethylene glycol (6.47 g, 8.63 mmol) having a molecular weight of 750, which was dissolved in anhydrous tetrahydrofuran (50 mL), was immediately added dropwise, and then the reaction was carried out at room temperature for 24 hours and at 40° C. to 50° C. for 24 hours.

Step 3: Thereafter, a solution, in which triethylamine (2.10 g, 15.10 mmol) was added to dry amino methoxypolyethylene glycol (3.24 g, 4.331 mmol) having a molecular weight of 750, which was dissolved in anhydrous tetrahydrofuran (50 mL), was additionally added dropwise to the reactant of Step 2, and then the reaction was further carried out at room temperature for 24 hours and at 40° C. to 50° C. for 24 hours.

The solution in which the reaction was completed was filtered in order to remove the produced triethylamine hydrochloride, and the reaction filtrate was concentrated under reduced pressure until only a small amount of solvent remained. The concentrated solution was dissolved in a small amount of methanol, placed in MWCO 12000 Membrane (Spectrum Laboratories, Inc.), dialyzed against methanol at room temperature for 5 days, and then dialyzed once more against distilled water for 5 days. Thereafter, the resultant was lyophilized, thereby obtaining a polyphosphazene polymer [NP(IleOEt)$_{1.21}$(AMPEG750)$_{0.51}$(aminoethanol)$_{0.28}$]$_n$ (7.21 g), which contains isoleucine ethyl ester, amino methoxypolyethylene glycol, and aminoethanol.

Step 4: The polyphosphazene polymer [NP(IleOEt)$_{1.21}$(AMPEG750)$_{0.51}$(aminoethanol)$_{0.28}$]$_n$ (11.32 g, 6.16 mmol), which was obtained from Step 3, was dissolved in tetrahydrofuran (200 mL), and then reacted at room temperature for 8 hours using 2 equivalents of succinic anhydride (1.23 g, 12.31 mmol) and 2 equivalents of dimethylaminopyridine (1.51 g, 12.31 mmol). The reaction filtrate was concentrated under reduced pressure, dissolved in a small amount of methanol, dialyzed against methanol at room temperature for 5 days, and then dialyzed against distilled water at 4° C. for 5 days. Thereafter, the resultant was lyophilized, thereby obtaining a polyphosphazene polymer [NP(IleOEt)$_{1.21}$(AMPEG750)$_{0.51}$(aminoethylsuccinate)$_{0.28}$]$_n$ (10.58 g), which contains isoleucine ethyl ester, amino methoxypolyethylene glycol, and aminoethylsuccinate.

Step 5: [NP(IleOEt)$_{1.21}$(AMPEG750)$_{0.51}$(aminoethylsuccinate)$_{0.28}$]$_n$ (4.5 g, 1.88 mmol) obtained from Step 4 was dissolved in dimethylformamide (90 mL), and 2 equivalents of diisopropylcarbodiimide (1.20 g) dissolved in anhydrous dimethylformamide (20 mL) were then added thereto. After 30 minutes, hydroxysuccinimide (0.43 g, 3.75 mmol) was likewise dissolved in dimethylformamide (15 mL), and added to the resultant. The reaction was then carried out at room temperature for 1 day. Thereafter, 2 equivalents of dopamine hydrochloride (0.84 g, 3.75 mmol) and diisopropylethylamine (2.27 g, 7.50 mmol) in dry DMF were added, and then reacted at room temperature for 48 hours. The reaction filtrate was placed in MWCO 12-14000 Membrane, dialyzed against distilled water at 4° C. for 5 days, and the resultant was lyophilized, thereby obtaining a final product [NP(IleOEt)$_{1.21}$(AMPEG750)$_{0.51}$(aminoethylsuccinate)$_{0.22}$(aminoethylsuccinateDN)$_{0.06}$]$_n$ (4.3 g).

Nuclear Magnetic Resonance Spectrum with Hydrogen (CDCl$_3$, ppm):
δ 0.7 to 1.1 (b, —NHCH(CH(C<u>H$_3$</u>)CH$_2$C<u>H$_3$</u>)OCH$_2$CH$_3$),
δ 1.1 to 1.3 (b, —NHCH(CH(CH$_3$)C<u>H$_2$</u>CH$_3$)OC<u>H$_2$</u>C<u>H$_3$</u>),
δ 1.4 to 1.8 (b, —NHC<u>H</u>(CH(CH$_3$)CH$_2$CH$_3$)OCH$_2$CH$_3$),
δ 1.9 (s, —NHCH$_2$CH$_2$OCOCH$_2$CONHCH$_2$CH$_2$O$_2$C(C<u>H$_3$</u>)C=CH$_2$),
δ 2.5 to 2.7 (b, —NHCH$_2$CH$_2$OCOCH$_2$CH$_2$CONHCH$_2$CH$_2$C$_6$H$_5$(OH)$_2$—NHCH$_2$CH$_2$OCOCH$_2$CH$_2$COOH),
δ 2.9 to 3.2 (b, —NHCH$_2$CH$_2$OCOCH$_2$CH$_2$CONHCH$_2$CH$_2$C$_6$H$_5$(OH)$_2$),
δ 3.4 (s, —NH(CH$_2$CH$_2$O)$_{17}$C<u>H$_3$</u>),
δ 3.4 to 3.8 (b, —NH(C<u>H$_2$C<u>H$_2$</u>O)$_{17}$CH$_3$),
δ 3.9 to 4.3 (b, —NHC<u>H</u>(CH(CH$_3$)CH$_2$CH$_3$)OC<u>H$_2$</u>CH$_3$, —NHCH$_2$CH$_2$OCOCH$_2$CH$_2$CONHCH$_2$CH$_2$C$_6$H$_5$(OH)$_2$),
δ 6.4 (s, —NHCH$_2$CH$_2$OCOCH$_2$CH$_2$CONHCH$_2$CH$_2$C$_6$H$_5$(OH)$_2$)
δ 6.6 (s, —NHCH$_2$CH$_2$OCOCH$_2$CH$_2$CONHCH$_2$CH$_2$C$_6$H$_5$(OH)$_2$)
δ 8.7 (s, —NHCH$_2$CH$_2$OCOCH$_2$CH$_2$CONHCH$_2$CH$_2$C$_6$H$_5$(OH)$_2$)
Average molecular weight (M$_w$): 28,184

Example 2: Preparation of Poly[(Isoleucine Ethyl Ester)$_{1.35}$(Amino Methoxypolyethylene Glycol 750)$_{0.39}$(Amino Ethylsuccinate)$_{0.14}$(Aminoethyl Dopamine)$_{0.12}$Phosphazene]$_n$ Step 1: Dry isoleucine ethyl ester hydrochloride (IleOEt.HCl, 22.46 g, 114.76 mmol) was dissolved in 300 mL of anhydrous tetrahydrofuran (THF), followed by addition of triethylamine (63.98 g, 459.05 mmol). Poly(dichlorophosphazene) (9.00 g, 77.66 mmol) dissolved in anhydrous tetrahydrofuran (100 mL) was added dropwise to the mixed solution in an acetone-dry ice bath at −60° C., and then gradually raised to room temperature, thereby reacting the resultant for 48 hours.

Step 2: After confirmation of the progress of the reaction in Step 1 while confirming $^{31}$P-NMR, dry aminoethanol (1.58 g, 25.89 mmol) was dissolved in anhydrous tetrahydrofuran (50 mL), and triethylamine was added thereto so that the resultant was added to the above reactant. Thereafter, a solution, in which triethylamine (13.35 g, 95.78 mmol) was added to dry amino methoxypolyethylene glycol (35.92 g, 47.89 mmol) having a molecular weight of 750, which was dissolved in anhydrous tetrahydrofuran (200 mL), was immediately added dropwise, and then the reaction was carried out at room temperature for 24 hours and at 40° C. to 50° C. for 24 hours.

Step 3: Thereafter, a solution, in which triethylamine (4.45 g, 31.93 mmol) was added to dry amino methoxypolyethylene glycol (11.97 g, 15.96 mmol) having a molecular weight of 750, which was dissolved in anhydrous tetrahydrofuran (80 mL), was additionally added dropwise to the reactant of Step 2, and then the reaction was further carried out at room temperature for 24 hours and at 40° C. to 50° C. for 24 hours.

The solution in which the reaction was completed was filtered in order to remove the produced triethylamine hydrochloride, and the reaction filtrate was concentrated under reduced pressure until only a small amount of solvent remained. The concentrated solution was dissolved in a small amount of methanol, placed in MWCO 12000 Membrane (Spectrum Laboratories, Inc.), dialyzed against methanol at room temperature for 5 days, and then dialyzed once more against distilled water for 5 days. Thereafter, the resultant was lyophilized, thereby obtaining a polyphosphazene polymer [NP(IleOEt)$_{1.35}$(AMPEG750)$_{0.39}$(aminoethanol)$_{0.26}$]$_n$ (23.46 g), which contains isoleucine ethyl ester, amino methoxypolyethylene glycol, and aminoethanol.

Step 4: The polyphosphazene polymer [NP(IleOEt)$_{1.35}$(AMPEG750)$_{0.39}$(aminoethanol)$_{0.26}$]$_n$ (23.46 g, 15.56 mmol), which was obtained from Step 3, was dissolved in tetrahydrofuran (400 mL), and then reacted at room temperature for 8 hours using 2 equivalents of succinic anhydride (2.60 g, 25.97 mmol) and 2 equivalents of dimethylaminopyridine (3.17 g, 25.97 mmol). The reaction filtrate was concentrated under reduced pressure, dissolved in a small amount of methanol, dialyzed against methanol at room temperature for 5 days, and then dialyzed against distilled water at 4° C. for 5 days. Thereafter, the resultant was lyophilized, thereby obtaining a polyphosphazene polymer [NP(IleOEt)$_{1.35}$(AMPEG750)$_{0.39}$(aminoethylsuccinate)$_{0.26}$]$_n$ (23.50 g), which contains isoleucine ethyl ester, amino methoxypolyethylene glycol, and aminoethylsuccinate.

Step 5: [NP(IleOEt)$_{1.35}$(AMPEG750)$_{0.39}$(aminoethylsuccinate)$_{0.26}$]$_n$ (9.5 g, 4.12 mmol) obtained from Step 4 was dissolved in dimethylformamide (180 mL), and 2 equivalents of diisopropylcarbodiimide (1.96 g, 8.23 mmol) dissolved in anhydrous dimethylformamide (40 mL) were then added thereto. After 30 minutes, hydroxysuccinimide (0.94 g, 8.23 mmol) was likewise dissolved in dimethylformamide (30 mL), and added to the resultant. The reaction was carried out at room temperature for 1 day. Thereafter, 2 equivalents of dopamine hydrochloride (1.56 g, 8.23 mmol) and diisopropylethylamine (2.87 g, 16.46 mmol) in dry DMF were added, and then reacted at room temperature for 48 hours. The reaction filtrate was placed in MWCO 12-14000 Membrane, dialyzed against distilled water at 4° C. for 5 days, and the resultant was lyophilized, thereby obtaining a final product [NP(IleOEt)$_{1.35}$(AMPEG750)$_{0.39}$(aminoethylsuccinate)$_{0.14}$(aminoethylsuccinateDN)$_{0.12}$]$_n$ (9.6 g).

Nuclear Magnetic Resonance Spectrum with Hydrogen (CDCl$_3$, Ppm):

δ 0.7 to 1.1 (b, —NHCH(CH(C$\underline{H_3}$)CH$_2$C$\underline{H_3}$)OCH$_2$CH$_3$),
δ 1.1 to 1.3 (b, —NHCH(CH(CH$_3$)C$\underline{H_2}$CH$_3$)OCH$_2$C$\underline{H_3}$),
δ 1.4 to 1.8 (b, —NHC$\underline{H}$(C$\underline{H}$(CH$_3$)CH$_2$CH$_3$)OCH$_2$CH$_3$),
δ 1.9 (s, —NHCH$_2$CH$_2$OCOCH$_2$CH$_2$CONHCH$_2$CH$_2$O$_2$C(C$\underline{H_3}$)C=CH$_2$),
δ 2.5 to 2.7 (b, —NHCH$_2$CH$_2$OCOCH$_2$CH$_2$CONHCH$_2$CH$_2$C$_6$H$_5$(OH)$_2$—NHCH$_2$CH$_2$OCOCH$_2$CH$_2$COOH),
δ 2.9 to 3.2 (b, —NHCH$_2$CH$_2$OCOCH$_2$CH$_2$CONHCH$_2$CH$_2$C$_6$H$_5$(OH)$_2$),
δ 3.4 (s, —NH(CH$_2$CH$_2$O)$_{17}$C$\underline{H_3}$),
δ 3.4 to 3.8 (b, —NH(C$\underline{H_2}$C$\underline{H_2}$O)$_{17}$CH$_3$),
δ 3.9 to 4.3 (b, —NHC$\underline{H}$(CH(CH$_3$)CH$_2$CH$_3$)OC$\underline{H_2}$CH$_3$, —NHCH$_2$CH$_2$OCOCH$_2$CH$_2$CONHCH$_2$CH$_2$C$_6$H$_5$(OH)$_2$),
δ 6.4 (s, —NHCH$_2$CH$_2$OCOCH$_2$CH$_2$CONHCH$_2$CH$_2$C$_6$H$_5$(OH)$_2$)
δ 6.6 (s, —NHCH$_2$CH$_2$OCOCH$_2$CH$_2$CONHCH$_2$CH$_2$C$_6$H$_5$(OH)$_2$)
δ 8.7 (s, —NHCH$_2$CH$_2$OCOCH$_2$CH$_2$CONHCH$_2$CH$_2$C$_6$H$_5$(OH)$_2$)

Average Molecular Weight ($M_w$): 35,121

Example 3: Preparation of Poly[(Isoleucine Ethyl Ester)$_{1.21}$(Amino Methoxypolyethylene Glycol 750)$_{0.51}$(Amino Ethylsuccinate)$_{0.20}$(Aminoethyl Dopamine)$_{0.08}$Phosphazene]$_n$ Step 1: Dry isoleucine ethyl ester hydrochloride (IleOEt.HCl, 9.79 g, 50.04 mmol) was dissolved in 100 mL of anhydrous tetrahydrofuran (THF), followed by addition of triethylamine (24.41 g, 175.17 mmol). Poly(dichlorophosphazene) (4.00 g, 34.52 mmol) dissolved in anhydrous tetrahydrofuran (50 mL) was added dropwise to the mixed solution in an acetone-dry ice bath at −60° C., and then gradually raised to room temperature, thereby reacting the resultant for 48 hours.

Step 2: After confirmation of the progress of the reaction in Step 1 while confirming $^{31}$P-NMR, dry aminoethanol (0.62 g, 10.35 mmol) was dissolved in anhydrous tetrahydrofuran (50 mL), and triethylamine was added thereto so that the resultant was added to the above reactant. Thereafter, a solution, in which triethylamine (4.21 g, 30.20 mmol) was added to dry amino methoxypolyethylene glycol (6.47 g, 8.63 mmol) having a molecular weight of 750, which was dissolved in anhydrous tetrahydrofuran (50 mL), was immediately added dropwise, and then the reaction was carried out at room temperature for 24 hours and at 40° C. to 50° C. for 24 hours.

Step 3: Thereafter, a solution, in which triethylamine (2.10 g, 15.10 mmol) was added to dry amino methoxypolyethylene glycol (3.24 g, 4.331 mmol) having a molecular weight of 750, which was dissolved in anhydrous tetrahydrofuran (50 mL), was additionally added dropwise to the reactant of Step 2, and then the reaction was further carried out at room temperature for 24 hours and at 40° C. to 50° C. for 24 hours.

The solution in which the reaction was completed was filtered in order to remove the produced triethylamine hydrochloride, and the reaction filtrate was concentrated under reduced pressure until only a small amount of solvent remained. The concentrated solution was dissolved in a small amount of methanol, placed in MWCO 12000 Membrane (Spectrum Laboratories, Inc.), dialyzed against methanol at room temperature for 5 days, and then dialyzed once more against distilled water for 5 days. Thereafter, the resultant was lyophilized, thereby obtaining a polyphosphazene polymer [NP(IleOEt)$_{1.19}$(AMPEG750)$_{0.55}$(aminoethanol)$_{0.25}$]$_n$ (7.21 g), which contains isoleucine ethyl ester, amino methoxypolyethylene glycol, and aminoethanol.

Step 4: The polyphosphazene polymer [NP(IleOEt)$_{1.21}$(AMPEG750)$_{0.51}$(aminoethanol)$_{0.25}$]$_n$ (11.32 g, 6.16 mmol), which was obtained from Step 3, was dissolved in tetrahydrofuran (200 mL), and then reacted at room temperature for 8 hours using 2 equivalents of succinic anhydride (1.23 g, 12.31 mmol) and 2 equivalents of dimethylaminopyridine (1.51 g, 12.31 mmol). The reaction filtrate was concentrated under reduced pressure, dissolved in a small amount of methanol, dialyzed against methanol at room temperature for 5 days, and then dialyzed against distilled water at 4° C. for 5 days. Thereafter, the resultant was lyophilized, thereby obtaining a polyphosphazene polymer [NP(IleOEt)$_{1.21}$(AMPEG750)$_{0.51}$(aminoethylsuccinate)$_{0.28}$]$_n$ (10.58 g), which contains isoleucine ethyl ester, amino methoxypolyethylene glycol, and aminoethylsuccinate.

Step 5: [NP(IleOEt)$_{1.21}$(AMPEG750)$_{0.51}$(aminoethylsuccinate)$_{0.2}$]$_n$ (2.93 g, 1.22 mmol) obtained from Step 4 was dissolved in dimethylformamide (80 mL), and 2 equivalents of diisopropylcarbodiimide (0.78 g) dissolved in anhydrous dimethylformamide (20 mL) were then added thereto. After 30 minutes, hydroxysuccinimide (0.28 g, 2.44 mmol) was likewise dissolved in dimethylformamide (15 mL), and added to the resultant. The reaction was then carried out at room temperature for 1 day. Thereafter, 2 equivalents of dopamine hydrochloride (0.55 g, 2.44 mmol) and diisopropylethylamine (1.48 g, 4.88 mmol) in dry DMF were added, and then reacted at room temperature for 48 hours. The reaction filtrate was placed in MWCO 12-14000 Membrane, dialyzed against distilled water at 4° C. for 5 days, and the resultant was lyophilized, thereby obtaining a final product [NP(IleOEt)$_{1.21}$(AMPEG750)$_{0.51}$(aminoethylsuccinate)$_{0.20}$(aminoethylsuccinateDN)$_{0.08}$]$_n$ (3.03 g).

Nuclear Magnetic Resonance Spectrum with Hydrogen (CDCl$_3$, Ppm):

δ 0.7 to 1.1 (b, —NHCH(CH(C$\underline{H_3}$)CH$_2$C$\underline{H_3}$)OCH$_2$CH$_3$), δ 1.1 to 1.3 (b, —NHCH(CH(CH$_3$)C$\underline{H_2}$CH$_3$)OCH$_2$C$\underline{H_3}$), δ 1.4 to 1.8 (b, —NHC$\underline{H}$(C$\underline{H}$(CH$_3$)CH$_2$CH$_3$)OCH$_2$CH$_3$), δ 1.9 (s, —NHCH$_2$CH$_2$OCOCH$_2$CH$_2$CONHCH$_2$CH$_2$O$_2$C(C$\underline{H_3}$)C═CH$_2$), δ 2.5 to 2.7 (b, —NHCH$_2$CH$_2$OCOCH$_2$CH$_2$CONHCH$_2$CH$_2$C$_6$H$_5$(OH)$_2$—NHCH$_2$CH$_2$OCOCH$_2$CH$_2$COOH), δ 2.9 to 3.2 (b, —NHCH$_2$CH$_2$OCOCH$_2$CH$_2$CONHCH$_2$CH$_2$C$_6$H$_5$(OH)$_2$), δ 3.4 (s, —NH(CH$_2$CH$_2$O)$_{17}$C$\underline{H_3}$), δ 3.4 to 3.8 (b, —NH(C$\underline{H_2}$C$\underline{H_2}$O)$_{17}$CH$_3$), δ 3.9 to 4.3 (b, —NHC$\underline{H}$(CH(CH$_3$)CH$_2$CH$_3$)OC$\underline{H_2}$CH$_3$, —NHCH$_2$CH$_2$OCOCH$_2$CH$_2$CONHCH$_2$CH$_2$C$_6$H$_5$(OH)$_2$), δ 6.4 (s, —NHCH$_2$CH$_2$OCOCH$_2$CH$_2$CONHCH$_2$CH$_2$C$_6$H$_5$(OH)$_2$)

δ 6.6 (s, —NHCH$_2$CH$_2$OCOCH$_2$CH$_2$CONHCH$_2$CH$_2$C$_6$H$_5$(OH)$_2$)

δ 8.7 (s, —NHCH$_2$CH$_2$OCOCH$_2$CH$_2$CONHCH$_2$CH$_2$C$_6$H$_5$(OH)$_2$)

Average Molecular Weight (M$_w$): 16,729

Example 4: Preparation of Poly[(Isoleucine Ethyl Ester)$_{1.26}$(Amino Methoxypolyethylene Glycol 750)$_{0.42}$(Amino Ethyladipic Acid)$_{0.285}$(Aminoethyl Dopamine)$_{0.035}$Phosphazene]$_n$ Steps 1 to 3: The reaction was carried out in the same manner as in Example 1.

Step 4: The reaction was carried out in the same manner as in Step 4 of Example 1 except that adipic anhydride was used instead of succinic anhydride, thereby obtaining a polyphosphazene polymer [NP(IleOEt)$_{1.26}$(AMPEG750)$_{0.42}$(aminoethyladipate)$_{0.32}$]$_n$, which contains isoleucine ethyl ester, amino methoxypolyethylene glycol, and aminoethyladipate.

Step 5: [NP(IleOEt)$_{1.26}$(AMPEG750)$_{0.42}$(aminoethyladipate)$_{0.32}$]$_n$ (0.4 g, 0.16 mmol) obtained from Step 4 was dissolved in dimethylformamide (100 mL), and 2 equivalents of diisopropylcarbodiimide (78 mg, 0.33 mmol) dissolved in anhydrous dimethylformamide (20 mL) were then added thereto. After 30 minutes, hydroxysuccinimide (37.8 mg, 0.33 mmol) was likewise dissolved in dimethylformamide (20 mL), and added to the resultant. The reaction was then carried out at room temperature for 1 day. Thereafter, 2 equivalents of dopamine hydrochloride (62.2 mg, 0.33 mmol) and diisopropylethylamine (114.3 g, 0.66 mmol) in dry DMF were added, and then reacted for 48 hours. The reaction filtrate was placed in MWCO 12-14000 Membrane, dialyzed against distilled water at 4° C. for 5 days, and the resultant was lyophilized, thereby obtaining a final product [NP(IleOEt)$_{1.26}$(AMPEG750)$_{0.42}$(aminoethyladipate)$_{0.285}$(aminoethyladipateDN)$_{0.035}$]$_n$ (0.5 g).

Nuclear Magnetic Resonance Spectrum with Hydrogen (CDCl$_3$, ppm):

δ 0.7 to 1.1 (b, —NHCH(CH(C$\underline{H_3}$)CH$_2$C$\underline{H_3}$)OCH$_2$CH$_3$), δ 1.1 to 1.3 (b, —NHCH(CH(CH$_3$)C$\underline{H_2}$CH$_3$)OCH$_2$C$\underline{H_3}$), δ 1.4 to 1.8 (b, —NHC$\underline{H}$(C$\underline{H}$(CH$_3$)CH$_2$CH$_3$)OCH$_2$CH$_3$), δ 1.9 (s, —NHCH$_2$CH$_2$OCOCH$_2$CH$_2$CH$_2$CONHCH$_2$CH$_2$O$_2$C(C$\underline{H_3}$)C═CH$_2$), δ 2.5 to 2.7 (b, —NHCH$_2$CH$_2$OCOCH$_2$CH$_2$CH$_2$CONHCH$_2$CH$_2$C$_6$H$_5$(OH)$_2$—NHCH$_2$CH$_2$OCOCH$_2$CH$_2$CH$_2$CH$_2$COOH), δ 2.9 to 3.2 (b, —NHCH$_2$CH$_2$OCOCH$_2$CH$_2$CH$_2$CONHCH$_2$CH$_2$C$_6$H$_5$(OH)$_2$), δ 3.4 (s, —NH(CH$_2$CH$_2$O)$_{17}$C$\underline{H_3}$), δ 3.4 to 3.8 (b, —NH(C$\underline{H_2}$C$\underline{H_2}$O)$_{17}$CH$_3$), δ 3.9 to 4.3 (b, —NHC$\underline{H}$(CH(CH$_3$)CH$_2$CH$_3$)OC$\underline{H_2}$CH$_3$, —NHCH$_2$CH$_2$OCOCH$_2$CH$_2$CH$_2$CH$_2$CONHCH$_2$CH$_2$C$_6$H$_5$(OH)$_2$), δ 6.4 (s, —NHCH$_2$CH$_2$OCOCH$_2$CH$_2$CH$_2$CONHCH$_2$CH$_2$C$_6$H$_5$(OH)$_2$)

δ 6.6 (s, —NHCH$_2$CH$_2$OCOCH$_2$CH$_2$CH$_2$CONHCH$_2$CH$_2$C$_6$H$_5$(OH)$_2$)

δ 8.7 (s, —NHCH$_2$CH$_2$OCOCH$_2$CH$_2$CH$_2$CONHCH$_2$CH$_2$C$_6$H$_5$(OH)$_2$)

Average Molecular Weight (M$_w$): 22,410

Example 5: Sol-Gel Change of Phosphazene-Based Polymer Containing Catechol Group According to Temperature Change The catechol group-containing phosphazene-based polymers according to Examples 1 to 4 were each dissolved in phosphate-buffered saline (pH 7.4) at 4° C. at a concentration of 10 wt %. Thereafter, the resultants were placed in a chamber of a viscometer (Brookfield DV-III+ Rheometer) equipped with the TC-501 automatic water distiller, and a sol-gel transition behavior was observed by setting a shear rate to 0.1 to 1.7 per second, and by raising a temperature by 0.04° C. per minute.

In FIG. 1, the state of the catechol group-containing phosphazene-based polymer at 25° C. and 37° C. according to Example 1 of the present invention was shown as photographs. As shown in FIG. 1, it was confirmed that the polymer of Example 1 of the present invention existed in a form where a solution is flowing at room temperature, but existed in a gel form at body temperature due to phase transition.

Figure 2:
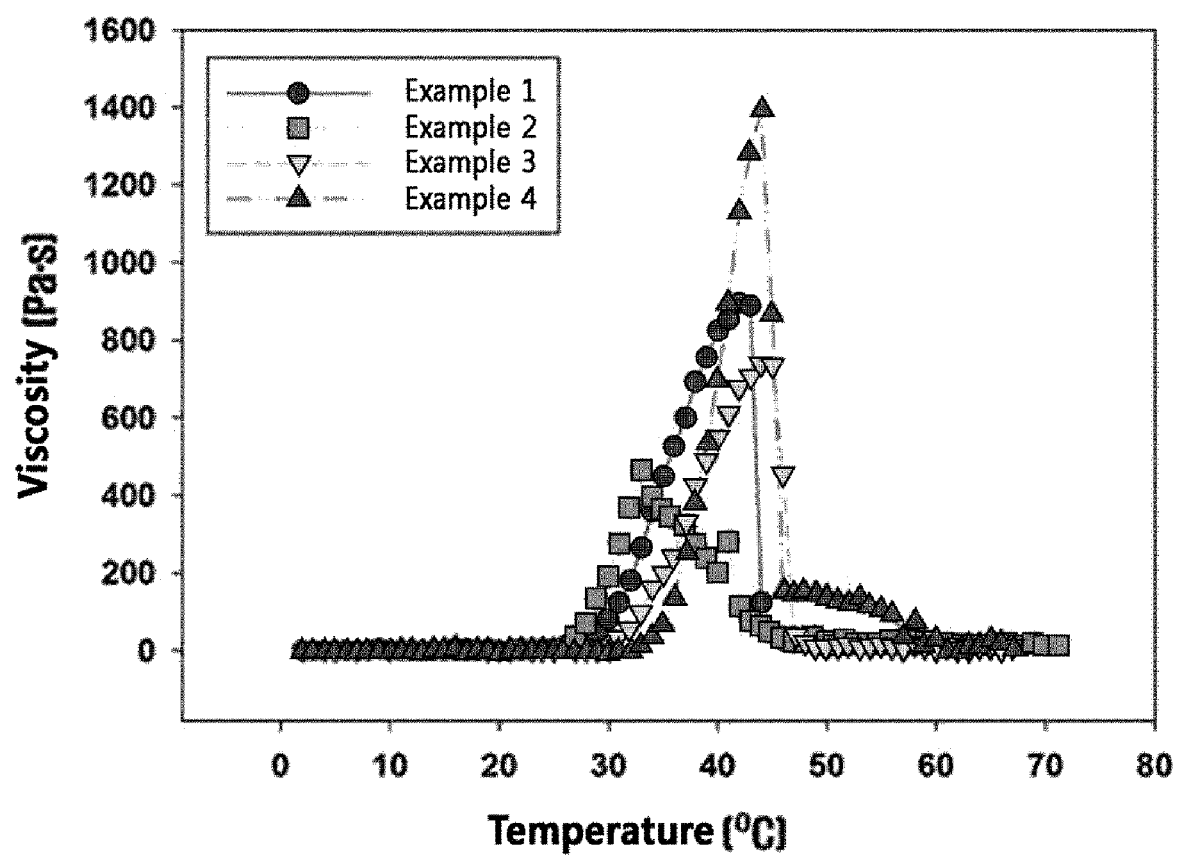
FIG. 2 is a graph showing a change in viscosity due to a temperature change of the catechol group-containing phosphazene-based polymer of the present invention.

The viscosities of the polymers of Examples 1 to 4 of the present invention according to temperature are shown in FIG. 2, and the gel properties thereof are shown in Table 1 below.

TABLE 1

| Polymer | Structure | Maximum gel temperature (° C.) | Maximum gel strength (Pa · s) |
|---|---|---|---|
| Example 1 | [NP(IleOEt)$_{1.21}$(AMPEG)$_{0.51}$(SA)$_{0.22}$(SADN)$_{0.06}$]$_n$ | 45 | 894 |
| Example 2 | [NP(IleOEt)$_{1.35}$(AMPEG)$_{0.39}$(SA)$_{0.14}$(SADN)$_{0.12}$]$_n$ | 36 | 463 |
| Example 3 | [NP(IleOEt)$_{1.21}$(AMPEG)$_{0.51}$(SA)$_{0.20}$(SADN)$_{0.08}$]$_n$ | 48 | 738 |
| Example 4 | [NP(IleOEt)$_{1.26}$(AMPEG)$_{0.42}$(AA)$_{0.255}$(AADN)$_{0.035}$]$_n$ | 45 | 1131 |

In Table 1 above, the maximum gel temperature indicates a temperature at which the viscosity of the polymer aqueous solution reaches the peak point, and the maximum gel strength indicates a viscosity measured at the maximum gel temperature above.

As shown in Table 1, even for the polymers (Examples 1 to 3) composed of the same substituents, it was confirmed that these have different maximum gel temperature and strength depending on the ratio of each substituent.

On the other hand, as shown in FIG. 2, the viscosity of all polymers of Examples 1 to 4 of the present invention started to increase at a temperature in the range of 25° C. to 35° C., which is below body temperature; that is, the polymers started to gelate. However, as shown in Table 1, each maximum viscosity and the temperature indicating the same were different depending on the polymer. This shows that it is possible for the polymers to exhibit sol-gel transition behavior within the desired range because the sol-gel transition can be regulated by changing the type of substituent and its composition from the phosphazene-based polymer.

Example 6: Change in Gel Amount of Phosphazene-Based Polymer Containing Catechol Group Depending on Time In order to confirm the change in gel amount depending on time, the catechol group-containing phosphazene-based polymers according to Examples 1 and 2 of the present invention were each dissolved in phosphate-buffered saline (pH 7.4) at 4° C. at a concentration of 10 wt %. Thereafter, 200 μL of the resultants were injected into mice's backs. After the day of injection, day 1, day 3, day 7, and day 14, respectively, these mice were sacrificed in order to obtain the gel, and the gel was visually observed to evaluate the reduction rate.

Figure 3:
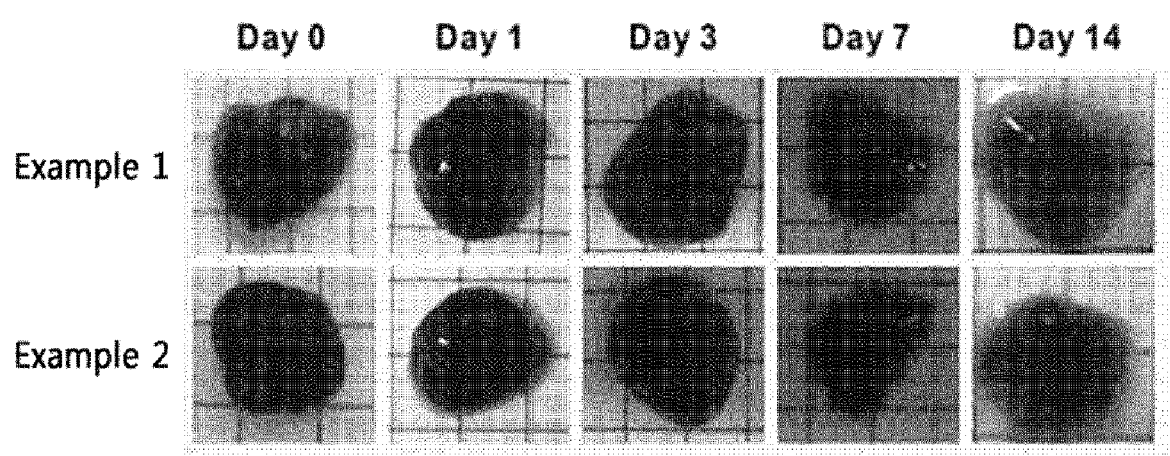
FIG. 3 is a photograph showing a decrease in the amount of gel of the catechol group-containing phosphazene-based polymer of the present invention according to the flow of time.

As shown in FIG. 3, it was confirmed that although the amount of gel decreased with the lapse of time after injection into the body, the gel injected into the body effectively remained in the injected tissues even after 2 weeks.

Figure 4:
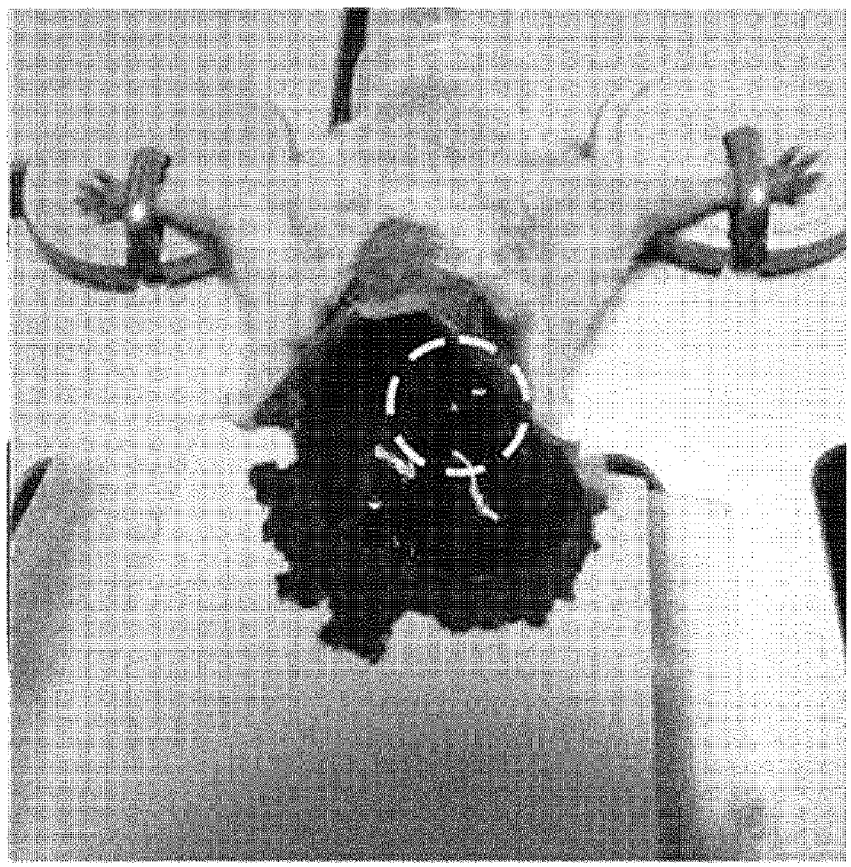
FIG. 4 is a photograph showing a tissue-adhesion ability of the catechol group-containing phosphazene polymer of the present invention in a rat model with liver puncture.

Example 7: Tissue-Adhesion Ability of Phosphazene-Based Polymer Hydrogel Containing Catechol Group In order to directly confirm a tissue-adhesion ability of the catechol group-containing phosphazene-based polymer according to the present invention, a hole was made on mice's livers to induce blood to flow out. Thereafter, the catechol group-containing phosphazene-based polymer solution according to Example 1 of the present invention was directly treated at the bleeding site, and the change in blood outflow amount was observed. Morphology of the damaged mice's livers treated with the catechol group-containing phosphazene-based polymer solution according to Example 1 of the present invention is shown in FIG. 4. In addition, the bleeding volume from the mice's livers treated with the catechol group-containing phosphazene-based polymer solution according to Examples 1 and 2 of the present invention was measured, and is shown in FIG. 5.

Figure 5:
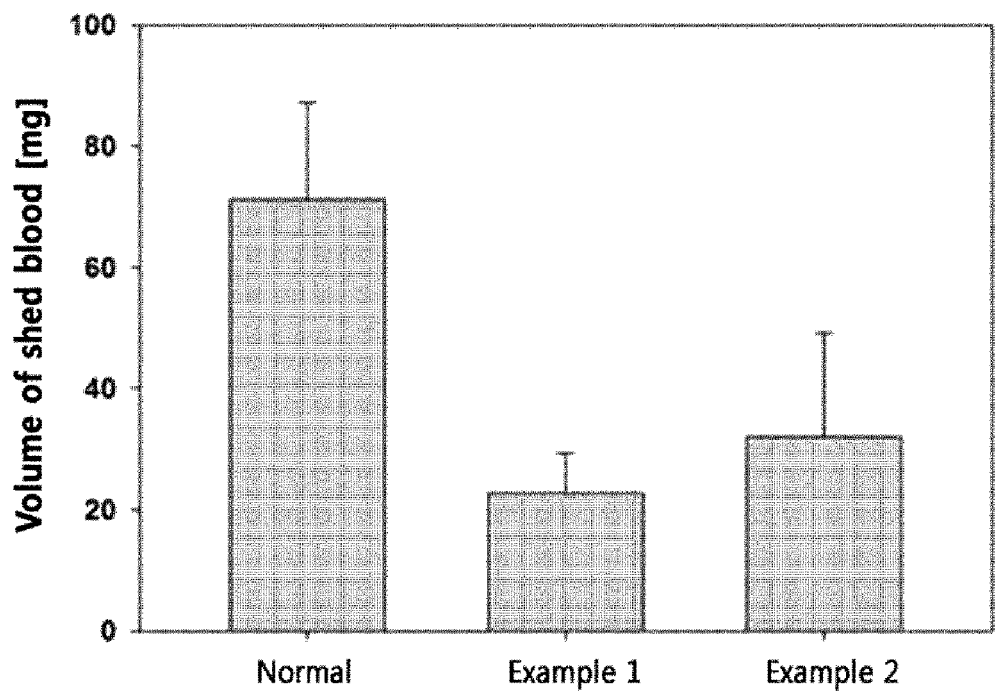
FIG. 5 is a graph showing a decrease in the amount of bleeding due to the catechol group-containing phosphazene-based polymer of the present invention in a rat model with liver puncture.

As shown in FIG. 5, it was confirmed that the bleeding volume was remarkably reduced when the damaged mice's livers were treated with the catechol group-containing phosphazene-based polymer solution according to Examples 1 and 2 of the present invention, compared with a control group in which the damaged mice's livers were not treated with any substance. This result indicates that the catechol group-containing phosphazene-based polymers according to the present invention have excellent tissue-adhesion ability, thereby effectively preventing bleeding from the wound site.

Example 8: Cytotoxicity of Phosphazene-Based Polymer Containing Catechol Group

Figure 6:
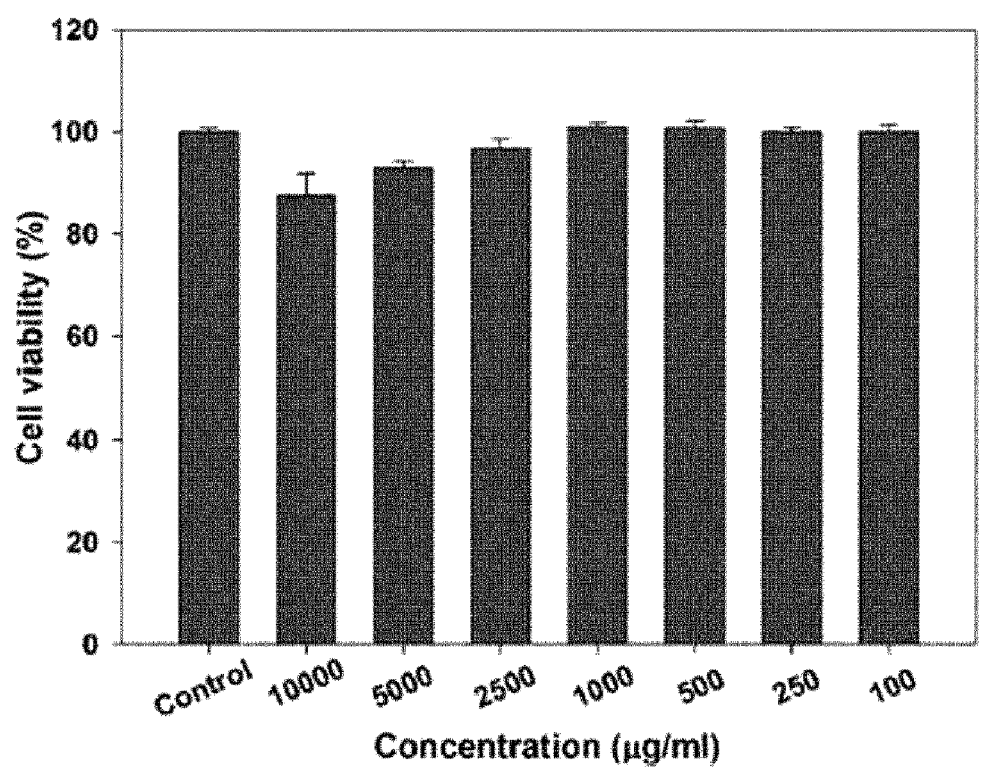
FIG. 6 is a graph showing cytotoxicity of the catechol group-containing phosphazene-based polymer of the present invention.

In order to ensure stability for in vivo application, cytotoxicity of the catechol group-containing phosphazene-based polymer according to the present invention was measured. Specifically, the polymer according to Example 1 of the present invention was treated with NIH3T3 cell line at a concentration of 100 μM to 10,000 μM, and cell viability thereof was observed. The result is shown in FIG. 6. NIH3T3 cells not treated with polymers are used as a control group. As shown in FIG. 6, even if the concentration of the polymer increased to 10,000 μM, the cell viability exhibited a high value of 85% or more. This result indicates that the polymers according to the present invention do not show toxicity to cells, and thus can be applied to the human body.

The invention claimed is:

1. A phosphazene-based polymer comprising a catechol group,
wherein, on a phosphorous atom of a polyphosphazene backbone represented by the following Formula 1,
a first moiety of an amino acid ester represented by the following Formula 2;
a second moiety of polyethylene glycol represented by the following Formula 3;
a third moiety comprising a functional group; and
a fourth moiety comprising a catechol group linked directly or by a linker to a part of or an entire functional group of the third moiety:

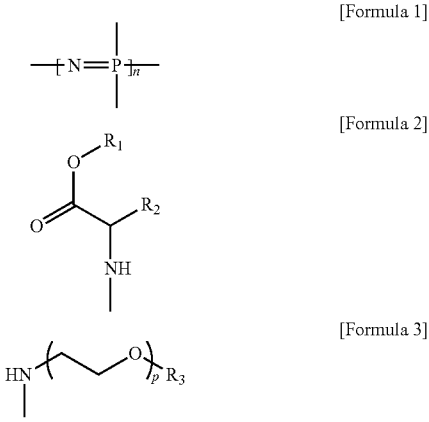

wherein,
the first moiety, the second moiety, the third moiety, and the fourth moiety are present in a molar ratio of a:b:c:d, respectively;
wherein a is 55 mol % to 77 mol %; b is 5 mol % to 30 mol %; a sum of c and d is 10 mol % to 20 mol %; and the c:d ratio is in a range of 1:0.1 to 1:1; and
wherein, in Formulas 1, 2, and 3,
$R_1$ is $C_{1-6}$ alkyl, $C_{1-6}$ alkenyl, or $C_{6-10}$ aryl-$C_{1-6}$ alkyl;
$R_2$ is hydrogen, methyl, isopropyl, 1-methylpropyl, 2-methylpropyl, thiomethyl, methylthioethyl, benzyl, hydroxylbenzyl, or 2-indolylmethyl;
$R_3$ is $C_{1-6}$ alkyl;
n is an integer of 3 to 100,000; and
p is an integer of 1 to 20.

2. The phosphazene-based polymer of claim 1, wherein the functional group is a hydroxy group or a carboxyl group.

3. The phosphazene-based polymer of claim 1, wherein $R_1$ is methyl, ethyl, propyl, butyl, benzyl, or 2-propenyl; and $R_3$ is methyl.

4. The phosphazene-based polymer of claim 1, further comprising a fifth moiety, in which at least one functional substance selected from the group consisting of a substance capable of regulating decomposition rate of a polymer, a substituent comprising an ionic group capable of regulating decomposition rate, a substituent capable of cross-linking, an additional compound capable of inducing tissue adhesion, a physiologically active substance, and a composite material formed by linear connection of two or more substances among them is linked directly or by a linker to a part of or an entire functional group of the third moiety.

5. The phosphazene-based polymer of claim 1, wherein the phosphazene-based polymer comprising a catechol group has a weight average molecular weight of 15,000 to 37,000, and is represented by the formula of poly[isoleucine ethyl ester]$_{a'}$(mino methoxypolyethylene glycol 750)$_{b'}$ (amino ethylsuccinate or amino ethyladipic acid)$_{c'}$(amino ethyldopamine)$_{d'}$phosphazene]$_{n'}$;

wherein, in the above formula, a' is from 1.20 to 1.36;

b' is from 0.37 to 0.53;

c' is from 0.13 to 0.26;

d' is from 0.03 to 0.13;

a'+b'+c'+d' is 2; and n' is an integer from 3 to 100,000.

6. A preparation method of the phosphazene-based polymer of claim 1, comprising:

a first step of reacting poly(dichlorophosphazene) of Formula 4 with an (amino acid)($C_{1-6}$ alkyl)ester of Formula 5;

a second step of reacting the reaction mixture obtained from the previous step by adding amino($C_{1-6}$ alkoxy) polyethylene glycol and amino($C_{1-6}$ alkanol);

a third step of reacting the reaction mixture of the previous step by further adding a amino($C_{1-6}$ alkoxy)polyethylene glycol solution dropwise;

a fourth step of reacting the product obtained from the previous step with $C_{1-6}$ alkanedioic acid or an anhydride thereof, and dimethylaminopyridine; and a fifth step of reacting the product obtained from the previous step with di($C_{1-6}$ alkyl)carbodiimide, hydroxysuccinimide, and dopamine:

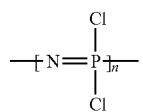

[Formula 4]

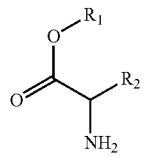

[Formula 5]

wherein, in Formulas 4 and 5, $R_1$, $R_2$, and n are as defined in claim 1.

7. The preparation method of claim 6, wherein the first to third steps are carried out in a tetrahydrofuran solution in the presence of triethylamine.

8. The preparation method of claim 6, wherein the first step is carried out for 24 hours to 60 hours while increasing a temperature from a range of −80° C. to −50° C. to a range of 10° C. to 50° C.

9. The preparation method of claim 6, wherein the second and third steps are independently carried out at 35° C. to 60° C. for 24 hours to 60 hours.

10. The preparation method of claim 6, further comprising a step of filtering the resulting reaction mixture; concentrating the filtrate under reduced pressure;
dissolving in methanol; and dialyzing the resulting concentrate with methanol and water after the reaction of the third step.

11. The preparation method of claim 6, wherein the fourth step is carried out in a dry tetrahydrofuran solution at 35° C. to 60° C. for 24 hours to 60 hours.

12. The preparation method of claim 6, further comprising a step of filtering the obtained reaction mixture; concentrating the filtrate under reduced pressure; dissolving in methanol; and dialyzing the resulting concentrate with methanol and water after the reaction of the fourth step.

13. The preparation method of claim 6, wherein the fifth step is carried out in a dry dimethylformamide solution at 10° C. to 35° C.

14. The preparation method of claim 6, wherein the fifth step is carried out by sequentially adding di($C_{1-6}$ alkyl) carbodiimide, hydroxysuccinimide, and dopamine while reacting for 10 minutes to 60 minutes, 6 hours to 24 hours, and 24 hours to 72 hours, respectively.

15. The preparation method of claim 6, wherein the (amino acid)($C_{1-6}$ alkyl)ester is isoleucine ethyl ester; the amino($C_{1-6}$ alkoxy)polyethylene glycol is amino methoxypolyethylene glycol; the amino($C_{1-6}$ alkanol) is aminoethanol; the $C_{1-6}$ alkanedioic acid or the anhydride thereof is succinic acid, glutaric acid, adipic acid, or an anhydride thereof; and the di($C_{1-6}$ alkyl)carbodiimide is diisopropylcarbodiimide.

16. A tissue-adhesive composition comprising a phosphazene-based polymer comprising a catechol group of claim 1 as an active ingredient.

17. The tissue-adhesive composition of claim 16, wherein the composition is used for wound healing, adhesion of surgical tissue, or hemostasis.

18. The tissue-adhesive composition of claim 16, wherein the composition is converted from a sol form to a gel form due to body temperature.

* * * * *